United States Patent [19]

Varma et al.

[11] 4,018,774
[45] Apr. 19, 1977

[54] STEROIDAL [16α,17-D]ISOXAZOLIDINES

[75] Inventors: Ravi K. Varma, Belle Mead;
Christopher M. Cimarusti,
Hamilton, both of N.J.

[73] Assignee: E. R. Squibb & Sons, Inc., Princeton, N.J.

[22] Filed: Feb. 13, 1976

[21] Appl. No.: 657,791

[52] U.S. Cl. .................. 260/239.55 R; 260/397.45
[51] Int. Cl.² ....................................... C07J 17/00
[58] Field of Search ............................. 260/239.55;
/Machine Searched Steroids

[56] References Cited
UNITED STATES PATENTS

| | | | |
|---|---|---|---|
| 3,340,255 | 9/1967 | Wagner-Jauregg | 260/239.55 |
| 3,349,084 | 10/1967 | Ayers et al. | 260/239.55 |

*Primary Examiner*—Elbert L. Roberts
*Attorney, Agent, or Firm*—Lawrence S. Levinson;
Merle J. Smith; Donald J. Barrack

[57] ABSTRACT

Novel steroids having the structure

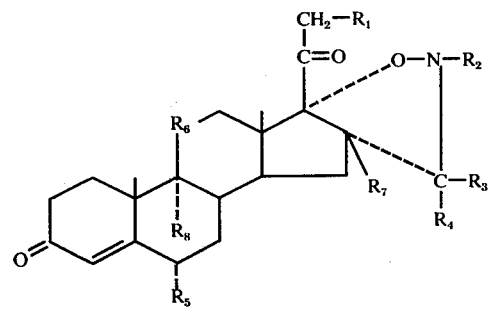

and the 1,2-dehydro derivatives thereof, wherein $R_1$ is hydrogen, hydroxy, alkanoyloxy, fluorine, chlorine, or bromine; $R_2$ is alkyl or aryl; $R_3$ is alkyl, aryl, alkanoyl, aroyl, alkoxycarbonyl, or cyano; $R_4$ is hydrogen, alkyl, or aryl; $R_5$ is hydrogen, fluorine or methyl; $R_6$ is carbonyl, β-hydroxymethylene, or β-chloromethylene; $R_7$ is hydrogen or methyl; and $R_8$ is fluorine or chlorine; have useful anti-inflammatory activity.

33 Claims, No Drawings

STEROIDAL [16α,17-D]ISOXAZOLIDINES

BACKGROUND OF THE INVENTION

Many 9-halo steroids of the pregnane series have found use as anti-inflammatory agents; see U.S. Pat. No. 2,852,511, issued Sept. 16, 958. Exemplary of the compounds having a 9-halo group that have reached the marketplace are triamcinolone (9-fluoro-11β, 16α, 17,21-tetrahydroxypregna-1,4-diene-3,20-dione), triamcinolone acetonide (9-fluoro-11β, 16α,17,21-tetrahydroxypregna-1,4-diene-3,20-dione, 16,17-acetonide) and halcinonide (21-chloro-9-fluoro-11β,16α,-17-trihydroxypregn-4-ene-3,20-dione, 16,17-acetonide).

Culbertson et al., *Journal of Heterocyclic Chemistry*, 1, 280 (1964), disclose the preparation of steroidal 16α,17α-fused isoxazolidines. The steroids disclosed by Culbertson et al. are of the pregnane series, but none of the steroids contains a 9-halo group, an 11-keto group, an 11β-hydroxy or an 11β-halo group. No utility is given for the steroids disclosed.

SUMMARY OF THE INVENTION

Steroids having the formula

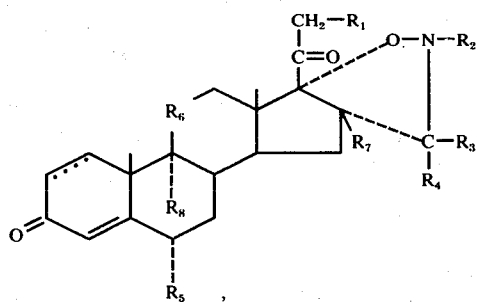

have been found to be useful topical and systemic anti-inflammatory agents. In formula I, and throughout the specification, the symbols are as described below:

$R_1$ is hydrogen, hydroxy, alkanoyloxy, fluorine, chlorine, or bromine;
$R_2$ is alkyl or aryl;
$R_3$ is alkyl, aryl, alkanoyl,

alkoxycarbonyl, or cyano;
$R_4$ is hydrogen, alkyl, or aryl;
$R_5$ is hydrogen, fluorine or methyl;
$R_6$ is carbonyl, β-hydroxymethylene, or β-chloromethylene;
$R_7$ is hydrogen or methyl; and
$R_8$ is fluorine or chlorine;
with the proviso that when $R_8$ is chlorine $R_6$ is β-chloromethylene;

The dotted line in the 1,2-position of the steroids of this invention represents the optional presence of ethylenic unsaturation.

The terms "alkyl" and "alkoxy", as used throughout the specification refer to groups having 1 to 6 carbon atoms.

The terms "alkanoyl" and "alkanoyloxy", as used throughout the specification, refer to groups having 1 to 7 carbon atoms.

The term "aryl", as used throughout the specification, refers to phenyl and phenyl substituted with halogen, nitro, cyano, or alkoxy groups; phenyl and monosubstituted phenyl are preferred,.

The term "halogen", as used throughout the specification, refers to fluorine, chlorine, bromine, and iodine; fluorine, chlorine, and bromine are preferred.

DETAILED DESCRIPTION OF THE INVENTION

The steroids of formula I are physicologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogential pruritus.

When given orally, the compounds of this invention may be used in a dosage range of 0.1 to 200 milligrams, preferably 0.3 to 100 milligrams. If administered topically, the compounds of this invention may be used in the range of 0.01 to 5.0% by weight, preferably 0.05 to 2.0% by weight, in a conventional cream or lotion.

The steroids of formula I wherein $R_1$ is other than hydroxy, $R_6$ is carbonyl or β-hydroxymethylene and $R_8$ is fluorine can be prepared by reacting a steroid having the formula

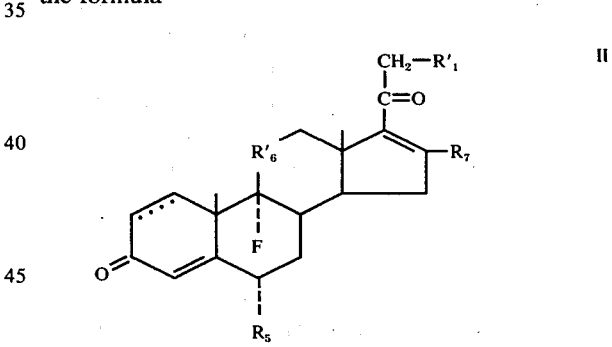

with a nitrone having the formula

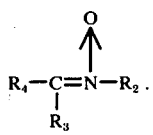

In formula II, and throughout the specification, the symbol $R'_1$ can be hydrogen, alkanoyloxy, fluorine, chlorine, or bromine, and the symbol $R'_6$ can be carbonyl or β-hydroxymethylene. The reaction can be run in an aprotic organic solvent, e.g., benzene or toluene, and while reaction conditions are not critical, the reaction will preferably be run under reflux conditions.

Those steroids of formula I wherein $R_6$ is β-chloromethylene can be prepared by first reacting a steroid having the formula

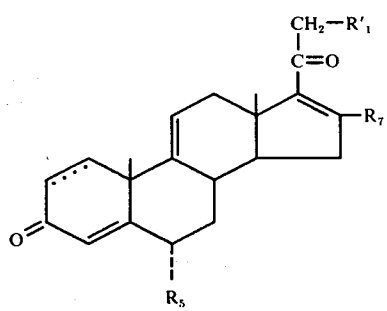

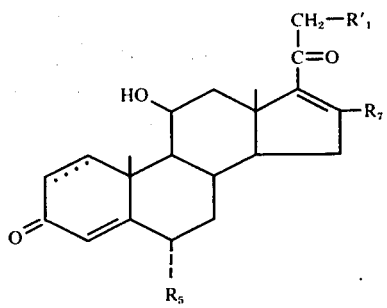

with a nitrone of formula III in an aprotic solvent to yield an intermediate having the formula

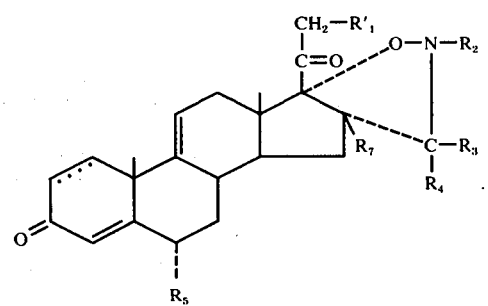

Saponification yields the corresponding 21-hydroxy steroid. The intermediates are novel, and as such, they constitute a part of this invention.

Reaction of a $\Delta^{9(11)}$-pregnene of formula V (or 21-hydroxy derivative thereof) with N-chlorosuccinimide or N-chloroacetamide and an acid of the formula

H—X,   (VI)

wherein X is chlorine or fluorine, yields a steroid of formula I wherein $R_6$ is $\beta$-chloromethylene. The reaction can be run in an organic solvent, e.g., glacial acetic acid, at a temperature of from about 0° C to 30° C.

Those steroids of formula I wherein $R_1$ is hydroxy can be prepared by saponification of a corresponding 21-alkanoyloxy steroid of formula I using procedures well known in the art.

The nitrones of formula III are readily prepared by any one of the many procedures known in the art. Exemplary procedures are disclosed in Chem. Revs., 64, 473 (1964); Quart. Revs., p. 329 (1966); Chem. Ber., 102, 1102, 1117, and 2346 (1969); Organic Functional Group Preparations, Vol. III, p. 301, Academic Press (1968); and Methoden der Organischen Chemie 10/4, p. 109 (1968).

The steroids of formulas II and IV are known in the art. The $\Delta^{9(11)}$-steroids of formula IV can be prepared by dehydration of a steroid having the formula Exemplary of the dehydration processes known in the steroid art are:
1. dehydration with phosphorous oxychloride and pyridine; and
2. dehydration with methanesulfonyl chloride and pyridine.

Additional methods for preparing the steroids of this invention will be apparent to a person of ordinary skill in the art of steroid chemistry. For example, a 21-halo steroid of formula I can be prepared from the corresponding 21-hydroxy steroid via a 21-alkane (or aryl) sulfonyl steroid using well-known procedures. Another example is the use of an 11$\beta$-acyloxy steroid starting material for the preparation of an 11$\beta$-hydroxy steroid product.

Steroids of formula I, and the 1,2-dehydro derivatives thereof, wherein $R_1$ is hydroxy, alkanoyloxy, or chloro are preferred.

Steroids of formula I having an 11$\beta$-hydroxy group are preferred.

Steroids of formula I wherein $R_5$ is hydrogen are preferred.

Steroids of formula I wherein $R_8$ is fluorine are preferred.

The following examples are specific embodiments of this invention.

EXAMPLE 1

21-(Acetyloxy)-9-fluoro-11$\beta$-hydroxy-2'-methyl-3,20-dioxopregna-1,4-dieno[16$\alpha$,17-d]isoxazolidine-3'-carboxylic acid, ethyl ester $\alpha$-Ethoxycarbonyl-N-Methyl Nitrone a. Ethyl glyoxylate Diethyl tartrate (24 g) is oxidized with lead tetra-acetate (58 g) in dry benzene (150 ml). Distillation affords an oil (12 g) which is a mixture of acetic acid and ethyl glyoxylate. This is used directly in the next step.

b. $\alpha$-Ethoxycarbonyl-N-Methyl Nitrone

The above mixture of ethyl glyoxylate and acetic acid (11.34 g, containing 70 mmol aldehyde) is dissolved in methanol (110 ml), N-methylhydroxylamine hydrochloride (5.8 g) and sodium acetate trihydrate (10.9 g) are added and the mixture is stirred at room temperature for 24 hours. It is then concentrated in vacuo, diluted with water and extracted with dichloromethane. The dichloromethane solution is then washed with a dilute sodium bicarbonate solution and water, dried over anhydrous magnesium sulfate, evaporated and distilled to afford $\alpha$-ethoxy-carbonyl-N-methyl nitrone as a colorless solid (5.0 g), boiling point 80°–85° C/0.4 mm of Hg., melting point 43°–49° C. This is a mixture of the syn- and anti-isomers on the basis of the nmr spectrum.

21-(Acetyloxy)-9-fluoro-11β-hydroxy-2'-methyl-3,20-dioxopregna-1,4-dieno[16α,17-d]isoxazolidine-3'-carboxylic acid, ethyl ester To a solution of 1.34 g of 21-(acetyloxy)-9-fluoro-11β-hydroxypregna-1,4,16-triene-3,16-triene-3,20-dione dissolved in 40 ml of hot toluene is quickly added 432 mg of α-ethoxycarbonyl-N-methyl nitrone. The solution is then refluxed under nitrogen for 8 hours, cooled and 30 ml of hexane is added. The separated solid is filtered, washed with cold toluene and dried in vacuo. This is dissolved in 2:3 hexane-chloroform and chromatographed on a 100 g-silica gel column. Elution with 2:3 hexane-chloroform and 1:4 hexane-chloroform give two isomers: Isomer A (1.2 g) and Isomer B (250 mg). Three recrystallizations of Isomer A from acetone-hexane give 720 mg of material, melting point 235°–236° C.

Anal. Calc'd. for $C_{28}H_{36}NFO_8$: C, 63.02; H, 63.02; H, 6.80; N, 2.63; F, 3.56. Found: C, 62.94; H, 6.82; N, 2.69; F, 3.67.

Two recrystallizations of Isomer B give 190 mg of material, melting point 245°–246° C.

Anal. Calc'd. for $c_{28}H_{36}FNO_8$: C, 64.02; H, 6.80; N, 2.63; F, 3.56. Found: C, 62.83; H, 6.82; N, 2.52; F, 3.31.

EXAMPLE 2

9-Fluoro-11β,21-dihydroxy-2'-methyl-3'-(4-nitrophenyl)pregna-1,4-dieno[16α,17-d]isoxazolidine-3,20-dione A solution of 1.8 g of 11β,21-bis(acetyloxy)-9-fluoro-pregna-1,4,16-triene-3,20-dione and 1.42 g of α-(4-nitrophenyl)-N-methyl nitrone in 100 ml of o-dichlorobenzene is stirred at 160° C for 74 hours under nitrogen. The o-dichlorobenzene is then distilled off under vacuum. The residue is dissolved in chloroform-hexane (3:2) and chromatographed on a 60 g -silica gel column. Elution with 3:2 chloroform-hexane and 4:1 chloroform-hexane gives 1.5 g of material which is the diacetate of the title compound. This is dissolved in a mixture of tetrahydrofuran (75 ml) and methanol (25 ml), a 10% potassium carbonate solution (1.5 ml) is added and the mixture is stirred under nitrogen at room temperature for 65 hours. The resulting solution is neutralized with 5% acetic acid and evaporated in vacuo. The slurry is diluted with water and extracted with chloroform. The chloroform solution is dried over anhydrous sodium sulfate and evaporated in vacuo to give 1.2 g of residue. This is dissolved in chloroform-hexane (9:1) and chromatographed on a 50 g-silica gel column. Elution with 1:9 hexane-chloroform and chloroform give 910 mg of material. Crystallization from acetone-hexane gives 68:0 mg of the title compound, melting point 259°–260° C.

Anal. Calc'd. for $C_{29}H_{33}FN_2O_7$: C, 64.43; H, 6.15; N, 5.15; F, 3.51. Found: C, 64.23; H, 5.86; N, 5.17; F, 3.41.

EXAMPLE 3

21-(Acetyloxy)-9-fluoro-11β-hydroxy-2'-methyl-3'-(4-nitrophenyl)-pregna-1,4-dieno[16α,17-d]isoxazolidine-3,20-dione A solution of 300 mg of 9-fluoro-11β,21-dihydroxy-2'-methyl-3'-(4-nitrophenyl)pregna-1,4-dieno[16α,17-d]isoxazolidine-3,20-dione and 0.2 ml of acetic anhydride in 10 ml of pyridine is stirred at room temperature under nitrogen for about 16 hours. The resulting solution is poured into cold 5% hydrochloric acid and extracted with chloroform. The chloroform solution is washed with water, dried over anhydrous sodium sulfate and evaporated in vacuo to give 350 mg of a foam. This is dissolved in 3:2 chloroform-hexane and chromatographed on a 25 g-silica gel column. Elutions with chloroform-hexane (3:2, 4:1 and 1:9) give 300 mg of material. Two crystallizations from acetone-hexane give 187 mg of the title compound, melting point 182°–185° C.

Anal. Calc'd. for $C_{31}H_{35}FN_2O_8$: C, 63.90; H, 6.06; N, 4.81; F, 3.26. Found: C, 63.67; H, 6.36; N, 4.65; F, 3.21.

EXAMPLE 4

21-(Acetyloxy)-9-fluoro-11β-hydroxy-2',16β-dimethyl-3,20-dioxo-pregna-1,4-dieno[16α,17-d]isoxazolidine-3'-carboxylic acid, ethyl ester A solution of 21-(acetyloxy)-9-fluoro-11β-hydroxy-16-methylpregne-1,4,16-triene-3,20-dione (100 mg) and α-ethoxy-carbonyl-N-methyl nitrone (152 mg) in dry toluene (6.0 ml) is refluxed under an atmosphere of nitrogen for 48 hours. The mixture is then cooled, diluted with chloroform, washed successively with 5% hydrochloric acid, a dilute sodium bicarbonate solution and water, dried and evaporated to a residue. From this the title compound is isolated by preparative thin layer chromatography (silica gel plates; developed with chloroform-methanol, 97:3). One crystallization from ethyl acetatehexane affords 57 mg of material, melting point 241°–242° C (dec.) (discoloration starts from 232° C).

EXAMPLE 5

21-Chloro-9-fluoro-1β-hydroxy-2'-methyl-3'-(4-nitrophenyl)-pregna-1,4-dieno[16α,17-d]isoxazolidine-3,20-dione

A.

9-Fluoro-11β,21-dihydroxy-2'-methyl-3'-(4-nitrophenyl)pregna-1,4-dieno[16α, 17-d]isoxazolidine-3,20-dione, 21-methanesulfonate A solution of 9-fluoro-11β,21-dihydroxy-2'-methyl-3'-(4-nitrophenyl)pregna-1,4-dieno[16α,17-d]isoxazolidine-3,20-dione (1 mmole) in pyridine (10 ml) is stirred in an ice bath for 5 hours with methanesulfonyl chloride (0.3 ml). The resulting solution is poured into 5% hydrochloric acid and is extracted with chloroform. The chloroform solution is washed with a dilute sodium bicarbonate solution and water, dried and evaporated to give the title compound.

B.

21-Chloro-9-fluoro-11β-hydroxy-2'-methyl-3'-(4-nitrophenyl) pregna-1,4-dieno[16α,17-d]isoxazolidine-3,20-dione A solution of the methanesulfonate (1 mmole) in dimethyl-formamide is refluxed with lithium chloride (500 mg) for 2 hours. The resulting mixture is cooled, poured into water and extracted with chloroform. The chloroform solution is washed with water, dried, evaporated and the residue is chromatographed over a column of silica gel to isolate the title compound.

EXAMPLES 6–13

Following the procedure of Example 1, but substituting the steroid listed in column I for 21-(acetyloxy)-9-fluoro-11β-hydroxypregna-1,4,16-triene-3,20-dione and the nitrone listed in column II for α-ethoxycarbonyl-N-methyl nitrone yields the steroid listed in column III.

21-(Acetyloxy)-9,11β-dichloro-6α-fluoro-2′-methyl-3,20-dioxopregna-1,4-dieno[16α,17-d]isoxazolidine-3′-carboxylic acid, ethyl ester A solution of 21-(acetyloxy)-6α-fluoro-2′-methyl-3,20-dioxopregna-1,4,9(11)-trieno[16α,17-d]isoxazolindine-3′-carboxylic acid, ethyl ester (2.0 mmole) and lithium chloride (1.0g) in 30 ml of glacial acetic acid is stirred at 0.°–5° C and N-chlorosuccinimide (2.2 mmole) is added followed by a solution of hydrogen chloride (2.6 mmole) in 5.0 ml of tetrahydrofuran. The resulting mixture is stirred at room temperature for 2.0 hours, poured into 400 ml of cold water and extracted

| Example | Column I | Column II | Column III |
|---|---|---|---|
| 6 | 21-(Acetyloxy)-6α,9-difluoro-11β-hydroxypregna-1,4,16-triene-3,20-dione | α-Benzoyl-N-methyl-nitrone | 21-(Acetyloxy)-3′-benzoyl-6α,9-difluoro-11β-hydroxy-2′-methylpregna-1,4-dieno-[16α,17-d]isoxazolidine-3,20-dione |
| 7 | 9-Fluoro-11β-hydroxy-6α-methyl-pregna-1,4,16-triene-3,20-dione | α-Cyano-α,N-diphenyl-nitrone | 9-Fluoro-11β-hydroxy-6α-methyl-3,20-dioxo-2′,3′-diphenylpregna-1,4-dieno[16α,17-d]-isoxazolidine-3′-carbonitrile |
| 8 | 21-(Acetyloxy)-9-fluoro-11β-hydroxypregna-1,4,16-triene-3,20-dione | α-(4-Methoxyphenyl)-N-methyl nitrone | 21-(Acetyloxy)-9-fluoro-11β-hydroxy-3′-(4-methoxyphenyl)-2′-methylpregna-1,4-dieno[16α,17-d]isoxazolidine-3,20-dione |
| 9 | 21-(Acetyloxy)-6α,9-difluoro-11β-hydroxypregna-1,4,16-triene-3,20-dione | α-(4-Chlorophenyl)-N-phenyl nitrone | 21-(Acetyloxy)-3′-(4-chlorophenyl)-6α,9-difluoro-11β-hydroxy-2′-phenylpregna-1,4-dieno[16α,17-d]isoxazolidine-3,20-dione |
| 10 | 9-Fluoropregna-4,16-diene-3,11,20-trione | α-Benzoyl-N-methyl-nitrone | 3′-Benzoyl-9-fluoro-2′-methylpregn-4-eno[16α,17-d]isoxazolidine-3,11,20-trione |
| 11 | 21-(Acetyloxy)-9-fluoro-11β-hydroxypregna-1,4,16-triene-3,20-dione | α-Acetyl-N-methyl-nitrone | 21-(Acetyloxy)-3′-acetyl-9-fluoro-11β-hydroxy-2′-methylpregna-1,4-dieno[16α,17-d]isoxazolidine-3,20-dione |
| 12 | 21-(Acetyloxy)-9-fluoro-11β-hydroxypregna-1,4,16-triene-3,20-dione | α-Phenyl-α,N-dimethyl-nitrone | 21-(Acetyloxy)-11β-hydroxy-9-fluoro-2′,3′dimethyl-3′-phenylpregna-1,4-dieno[16α,17-d]isoxazolidine-3,20-dione |
| 13 | 9-Fluoropregna-4,16-diene-3,11,20-trione | α,α,N-Trimethylnitrone | 9-Fluoro-2′,3′,3′-trimethylpregn-4-eno-[16α,17-d]isoxazolidine-3,11,20-trione |

EXAMPLE 14

9.21-Difluoro-11β-hydroxy-2′-methyl-3′-(4-nitrophenyl)-pregna-1,4-dieno[16α,17-d]isoxazolidine-3,20-dione A solution of 9-fluoro-11β,21-dihydroxy-2′-methyl-3′-(4-nitrophenyl)pregna-1,4-dieno[16α,17-d]isoxazolidine-3,20-dione, 21-methanesulfonate (1 mmole, prepared as described in Example 5A) in dimethylformamide is refluxed with lithium fluoride (400 mg) for 2.0 hours. The resulting mixture is cooled, poured into water and extracted with chloroform. The chloroform solution is washed with water, dried, evaporated and the residue is chromatographed over silica gel to isolate the title compound.

EXAMPLE 15

21-(Acetyloxy)-9,11β-fluoro-2′-methyl-3,20-dioxopregna-1,4-dieno[16α,17-d]isoxazolidine-3′-carboxylic acid, ethyl ester

A.

21-(Acetoxy)-6α-fluoro-2′-methyl-3,20-dioxopregna-1,4,9(11)-trieno[16α,17-d]isoxazolidine-3′-carboxylic acid, ethyl ester A solution of 21-(acetyloxy)-6α-fluoropregna-1,4,9(11),16-tetraene-3,20-dione (2.0 mmole) and α-ethoxycarbonyl-N-methyl-nitrone (2.5 mmole) is refluxed in 30 ml of toluene under nitrogen for 8 hours. The mixture is then cooled, diluted with chloroform and subjected to column chromatography over silica gel to isolate the title compound.

with chloroform. The chloroform extract is washed with a dilute sodium bicarbonate solution and water, dried and evaporated. The residue is subjected to column chromatography over silica gel to isolate the title compound.

EXAMPLE 16

11β-Chloro-3′-(4-chlorophenyl)-9-fluoro-2′,6α-dimethylpregna-1,4-dieno[16α,17-d]isoxazolidine-3,20-dione

A.

3′-(4-Chlorophenyl)-2′,6α-dimethylpregna-1,4,9(11)-trieno-[16α,17-d]isoxazolidine-3,20dione A solution of 6α-methylpregna-1,4,9(11),16-tetraene-3,20-dione (2.0 mmole) and α-(4-chlorophenyl)-N-methylnitrone (2.5 mmole) in 50 ml of dry o-dichlorobenzene is heated in a bath at 160° C under nitrogen for 3 days. The mixture is then cooled, diluted with chloroform and chromatographed over silica gel to isolate the title compound.

B.

11β-Chloro-3′-(4-chlorophenyl)-9-fluoro-2′,6α-dimethylpregna-1,4-dieno[16α,17-d]isoxazolidine-3,20-dione A suspension of 3′-(4-clorophenyl)-2′,6α-dimethylpregna-1,4,9(11)-trieno[16α,17-d]isoxazolidine-3,20-dione (4.0 mmole) and N-chloroacetamide (4.4 mmole) in 60 ml of dry dichloromethane is added in the course of 5.0 minutes to a mixture of anhydrous hydrogen fluoride (24 g) in 40 ml of dry tetrahydrofuran in a polyethylene bottle at −78° C. After 1.0 hour, the mixture is maintained at 0° C for an additional 1.0 hour and is then poured into ice-cold dilute sodium bicarbonate solution. Extraction with dichloromethane followed by column chromatography yields the title compound.

What is claimed is:
1. A steroid having the formula

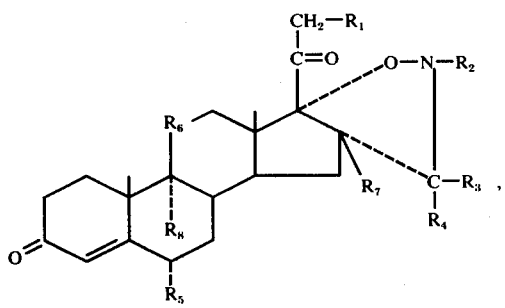

or a 1,2-dehydro derivative thereof, wherein $R_1$ is hydrogen, hydroxy, alkanoyloxy, fluorne, chlorine or bromine; $R_2$ is alkyl or aryl; $R_3$ is alkyl, aryl, alkanoyl,

alkoxy-carbonyl or cyano; $R_4$ is hydrogen, alkyl or aryl; $R_5$ is hydrogen, fluorine or methyl; $R_6$ is carbonyl, $\beta$-hydroxy-methylene, or $\beta$-chloromethylene; $R_7$ is hydrogen or methyl; and $R_8$ is fluorine or chlorine; with the proviso that when $R_8$ is chlorine $R_6$ is $\beta$-chloromethylene; wherein alkyl and alkoxy refer to groups having 1 to 6 carbon atoms; wherein alkanoyl refers to a group having 1 to 7 carbon atoms; and wherein aryl refers to phenyl and phenyl substituted with halogen, nitro, cyano, or alkoxy.

2. A steroid in accordance with claim 1 wherein $R_1$ is hydrogen.
3. A steroid in accordance with claim 1 wherein $R_1$ is hydroxy.
4. A steroid in accordance with claim 1 wherein $R_1$ is alkanoyloxy.
5. A steroid in accordance with claim 1 wherein $R_1$ is bromine.
6. A steroid in accordance with claim 1 wherein $R_1$ is chlorine.
7. A steroid in accordance with claim 1 wherein $R_1$ is fluorine.
8. A steroid in accordance with claim 1 wherein $R_2$ is alkyl.
9. A steroid in accordance with claim 1 wherein $R_2$ is aryl.
10. A steroid in accordance with claim 1 wherein $R_3$ is alkyl.
11. A steroid in accordance with claim 1 wherein $R_3$ is aryl.
12. A steroid in accordance with claim 1 wherein $R_3$ is alkanoyl.
13. A steroid in accordance with claim 1 wherein is

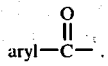

14. A steroid in accordance with claim 1 wherein $R_3$ is alkoxycarbonyl.
15. A steroid in accordance with claim 1 wherein $R_3$ is cyano.
16. A steroid in accordance with claim 1 wherein $R_4$ is hydrogen.
17. A steroid in accordance with claim 1 wherein $R_4$ is alkyl.
18. A steroid in accordance with claim 1 wherein $R_4$ is aryl.
19. A steroid in accordance with claim 1 wherein $R_5$ is hydrogen.
20. A steroid in accordance with claim 1 wherein $R_5$ is methyl.
21. A steroid in accordance with claim 1 wherein $R_5$ is fluorine.
22. A steroid in accordance with claim 1 wherein $R_6$ is carbonyl.
23. A steroid in accordance with claim 1 wherein $R_6$ is $\beta$-hydroxymethylene.
24. A steroid in accordance with claim 1 wherein $R_6$ is $\beta$-chloromethylene.
25. A steroid in accordance with claim 1 wherein $R_7$ is hydrogen.
26. A steroid in accordance with claim 1 wherein $R_7$ is methyl.
27. A steroid in accordance with claim 1 wherein $R_8$ is fluorine.
28. A steroid in accordance with claim 1 wherein $R_8$ is chlorine.
29. The steroid in accordance with claim 1 having the name 21-(acetyloxy)-9-fluoro-11$\beta$-hydroxy-2'-methyl-3,20-dioxopregna-1,4-dieno[16$\alpha$,17-d]isoxazolidine-3'-carboxylic acid, ethyl ester.
30. The steroid in accordance with claim 1 having the name 9-fluoro-11$\beta$,21-dihydroxy-2'-methyl-3'-(4-nitrophenyl)-pregna-1,4-dieno[16$\alpha$,17-d]isoxazolidine-3,20-dione.
31. The steroid in accordance with claim 1 having the name 21-(acetyloxy)-9-fluoro-11$\beta$-hydroxy-2'-methyl-3'-(4-nitrophenyl)pregna-1,4-dieno[16$\alpha$,17-d]isoxazolidine-3,20-dione.
32. The steroid in accordance with claim 1 having the name 21-(acetyloxy)-9-fluoro-11$\beta$-hydroxy-2',16$\beta$-dimethyl-3,20-dioxopregna-1,4-dieno[16$\alpha$,17-d]isoxazolidine-3'-carboxylic acid, ethyl ester.
33. A steroid having the formula

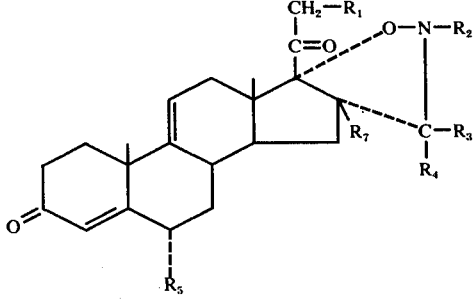

or a 1,2-dehydro derivative thereof, wherein $R_1$ is hydrogen, hydroxy, alkanoyloxy, fluorine, chlorine or bromine; $R_2$ is alkyl or aryl; $R_3$ is alkyl, aryl, alkanoyl,

alkoxycarbonyl, or cyano; $R_4$ is hydrogen, alkyl or aryl; $R_5$ is hydrogen, fluorine, or methyl; and $R_7$ is hydrogen or methyl; wherein alkyl and alkoxy refer to groups having 1 to 6 carbon atoms; wherein alkanoyl refers to a group having 1 to 7 carbon atoms; and wherein aryl refers to phenyl and phenyl substituted with halogen, nitro, cyano or alkoxy.

* * * * *

UNITED STATES PATENT AND TRADEMARK OFFICE
CERTIFICATE OF CORRECTION

PATENT NO. : 4,018,774
DATED : April 19, 1977
INVENTOR(S) : Ravi K. Varma et al.

It is certified that error appears in the above—identified patent and that said Letters Patent are hereby corrected as shown below:

Column 1, line 7, "Sept. 16, 958" should read
-- Sept. 16, 1958 --.

Column I, line 44, "described" should read
-- defined --.

Column 3, line 65, "p. 109" should read
-- p. 309 --.

Column 5, line 10, please omit "3,16-triene-".

Column 5, line 25, please omit "H, 63.02;".

Column 5, line 30, "C, 64.02;" should read
-- C, 63.02; --.

Column 5, line 39, "fluro-" should read
-- fluoro- --.

Column 6, line 31, "16-methylpregne" should read
-- 16-methylpregna --.

UNITED STATES PATENT OFFICE
CERTIFICATE OF CORRECTION

Patent No. 4,018,774          Dated April 19, 1977

Inventor(s) Ravi K. Varma et al.          Page 2 of 2

It is certified that error appears in the above-identified patent and that said Letters Patent are hereby corrected as shown below:

Column 7, line 59, "21-(Acetoxy)-" should read
-- 21-(Acetyloxy)- --.

Column 9, line 24, "fluorne" should read
-- fluorine --.

Signed and Sealed this thirtieth Day of August 1977

[SEAL]

Attest:

RUTH C. MASON
Attesting Officer

C. MARSHALL DANN
Commissioner of Patents and Trademarks